(12) United States Patent
Casagrande et al.

(10) Patent No.: US 6,595,684 B1
(45) Date of Patent: Jul. 22, 2003

(54) SYSTEM AND METHOD FOR EVALUATING A STRUCTURE

(75) Inventors: Louis Gregory Casagrande, Summit, NJ (US); George William Gilchrist, Massapequa, NY (US)

(73) Assignee: Northrop Grumman Corporation, Los Angeles, CA (US)

( * ) Notice: Subject to any disclaimer, the term of this patent is extended or adjusted under 35 U.S.C. 154(b) by 0 days.

(21) Appl. No.: 09/433,535

(22) Filed: Nov. 3, 1999

(51) Int. Cl.[7] ............................................... G01N 25/72
(52) U.S. Cl. ................................................ 374/5; 374/4
(58) Field of Search ............................ 374/4, 5, 6, 7

(56) References Cited

U.S. PATENT DOCUMENTS

| | | | |
|---|---|---|---|
| 3,396,335 A | 8/1968 | Burr et al. ..................... 324/51 |
| 4,232,554 A | 11/1980 | Aleck ............................. 73/577 |
| 4,620,799 A | 11/1986 | Palazzetti et al. .............. 374/5 |
| 4,854,162 A | 8/1989 | Yerace et al. ................. 73/119 |
| 5,032,727 A | 7/1991 | Cox et al. ...................... 250/330 |
| 5,294,198 A | * 3/1994 | Schlagcek ...................... 374/4 |
| 5,306,088 A | 4/1994 | Zoerner ....................... 374/131 |
| 5,370,943 A | * 12/1994 | Bruck et al. ................ 219/552 |
| 5,504,017 A | 4/1996 | Yue et al. ...................... 437/8 |
| 5,567,051 A | 10/1996 | Annati et al. ................. 374/57 |
| 5,654,977 A | 8/1997 | Morris ........................... 374/4 |
| 5,775,806 A | * 7/1998 | Allred ............................ 374/5 |
| 5,808,303 A | * 9/1998 | Schlagheck et al. ........... 374/4 |
| 5,984,522 A | * 11/1999 | Koizumi ................. 250/559.34 |
| 5,984,524 A | * 11/1999 | Teshirogi et al. .............. 374/5 |
| 6,033,107 A | * 3/2000 | Farina et al. ............... 374/161 |
| 6,146,014 A | * 11/2000 | Bruce et al. ................... 374/4 |

* cited by examiner

*Primary Examiner*—Diego Gutierrez
*Assistant Examiner*—Yaritza Guadalupe
(74) *Attorney, Agent, or Firm*—Baker Botts L.L.P.

(57) ABSTRACT

In a system (10) for evaluating a structure (20), the structure (20) has a predetermined baseline thermal signature. The system (10) includes a thermal source (30) located at least partially inside the structure (20). The thermal source (30) is operable to generate a predetermined amount of heat, which heats the structure (20). The system (10) also includes a detection device (40) that is operable to determine the temperature at various points of the structure (20). The system (10) further includes a computer (50) that is coupled to the detection device (40). The computer (50) is operable to generate a thermal signature of the structure (20) based on the temperature at the various points. The generated thermal signature of the structure (20) is compared to the baseline thermal signature of the structure (20) to determine whether anomalies exist in the structure (20).

22 Claims, 2 Drawing Sheets

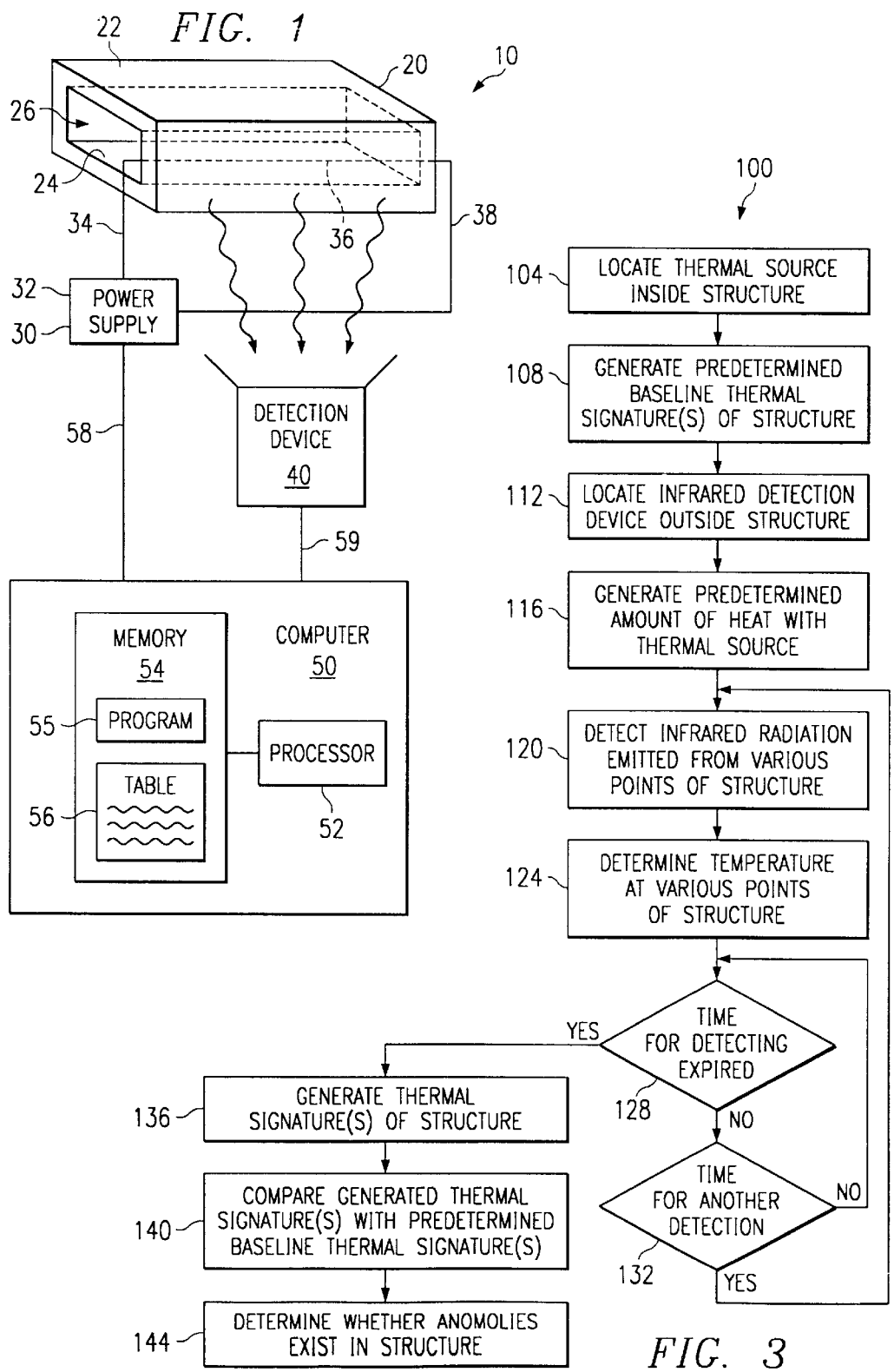

SYSTEM AND METHOD FOR EVALUATING A STRUCTURE

TECHNICAL FIELD OF THE INVENTION

This invention relates generally to the field of structures and, more specifically, to a system and method for evaluating a structure.

BACKGROUND OF THE INVENTION

The integrity of many structures, such as aircraft parts, which can be composed of metal, plastic, or composite, can be degraded by the presence of defects as well as the effects of age and wear. Defects can include cracks, delaminations, voids, or corrosion and are a prelude to structural failure. Thus, early detection of defects is a significant advantage. Unfortunately, defects can be buried deep within a structure, hidden in complex structures, or in their incipiency, making them difficult to detect without highly intrusive measures, which can damage the structure.

Currently, active source thermography is used to detect such defects in structures. In this process, a strong thermal pulse is directed at the outside surface of a structure, and the resulting temporal evolution of the surface heat signature is measured. The presence, size, and types of defects can be determined by analyzing the evolution of the surface thermal signature with knowledge of the physical thermal properties of the materials present because defects within the structure perturb the flow of heat compared with an idealized structure. The thermal pulse for this process is generally provided by a flash-lamp, and the surface temperatures are mapped using time resolved infrared imaging.

This technique, however, only works well for detecting defects in the flat, two dimensional surface of the structure. Thus, for deeply buried defects, complex structures, or incipient defects, an externally applied thermal pulse does not provide sufficient sensitivity. Better methods are needed, therefore, to detect defects buried in structures, in complex structures, or in their incipiency, before the onset of structural failure.

SUMMARY OF THE INVENTION

In accordance with the present invention, a method and system for evaluating a structure are provided that substantially eliminate or reduce at least some of the disadvantages and problems associated with previously developed systems and methods.

A system for evaluating a structure is disclosed. In this system, the structure to be evaluated has a predetermined baseline thermal signature. The system includes a thermal source located at least partially inside the structure. The thermal source is operable to generate a predetermined amount of heat, which heats the structure. The system also includes a detection device that is operable to determine the temperature at various points of the structure. The system further includes a computer that is coupled to the detection device. The computer is operable to generate a thermal signature of the structure based on the temperature at the various points of the structure. The generated thermal signature is compared to the baseline thermal signature to determine whether anomalies exist in the structure.

A method for evaluating a structure is also disclosed. The method includes five steps. Step one calls for locating a thermal source at least partially inside a structure to be evaluated. Step two requires generating a predetermined amount of heat with the thermal source. The third step calls for determining the temperature at various points of the structure. In step four, the method calls for generating a thermal signature of the structure based on the temperature at the various points of the structure. The final step of the method calls for comparing the generated thermal signature of the structure to a predetermined baseline thermal signature of the structure.

A technical advantage of the present invention is that heat from the thermal source is transferred to the inside of the structure. Thus, defects that are buried deep within the structure or hidden from the outside by other components of the structure can be heated. Therefore, because these defects affect the thermal signature of the structure, analyzing the thermal signature of the structure due to this type of heating enhances the probabilities of detecting a defect. Another technical advantage is that the amount of heat transferred to the structure by the thermal source can be accurately controlled. This ability provides for a more accurate determination of the defects in the structure, compared to an externally applied thermal pulse. In addition, this ability allows incipient defects to be identified. Moreover, accurate control of the heat transferred to the structure helps to ensure that the structure is not damaged by the evaluation. Other technical features and advantages will be readily apparent to those skilled in the art.

BRIEF DESCRIPTION OF THE DRAWINGS

For a more complete understanding of the present invention, and for further features and advantages, reference is now made to the following description, taken in conjunction with the accompanying drawings, in which:

FIG. 1 illustrates an embodiment of a system for evaluating a structure;

FIG. 3 is a flowchart demonstrating one method for evaluating a structure in accordance with the present invention.

DETAILED DESCRIPTION OF THE DRAWINGS

Figure 2A:
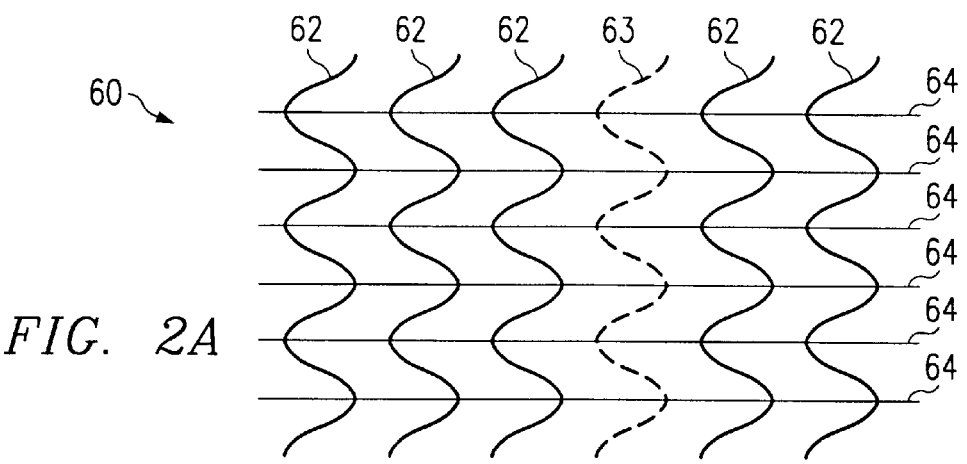
FIG. 2A illustrates one configuration of the structure that can be readily evaluated.

FIG. 1 illustrates an embodiment of a system 10 for evaluating a structure 20. In this embodiment, system 10 includes a thermal source 30, a detection device 40, and a computer 50. Thermal source 30 is located at least partially inside structure 20 and is coupled to computer, 50 by a link 58. Computer 50 is also coupled to detection device 40, by a link 59.

In operation, computer 50 commands thermal source 30 to generate a predetermined amount of heat, which is transferred to structure 20. The heating of structure 20 causes it to emit radiant energy. Detection device 40 detects the radiant energy emitted from structure 20 and determines the temperature at various points of structure 20 based on the energy detected. Using the temperature determined at various points of structure 20 by detection device 40, computer 50 generates a thermal signature of structure 20. The generated thermal signature of structure 20 can be compared to a predetermined baseline thermal signature of structure 20 to determine whether anomalies, such as defects, exist in structure 20. The thermal signatures of structure 20 can consist of the compilation of the temperatures at the various points of structure 20, a graphic representation of the temperatures at the various points wherein in the temperatures are represented by colors, or any other representation of the heat in structure 20.

In more detail, structure 20 includes an outer surface 22 and an interior surface 24. Interior surface 24 defines a passage 26 in structure 20. In addition, thermal source 30 includes a power supply 32 that supplies power to a thermal line 36, which transfers heat to structure 20. Thermal line 36 is located at least partially inside structure 20. Power supply 32 is coupled to thermal line 36 by a supply line 34 and a supply line 38. Power supply 32 is also coupled to computer 50, by link 58. Computer 50 controls the operations of power supply 32. Computer 50 includes a processor 52 and a memory 54. A program 55 in memory 54 specifies the operations for computer 50 to control system 10 for evaluating structure 20. A table 56 in memory 54 contains at least one predetermined thermal signature of structure 20 and can store the thermal signature determined during an evaluation controlled by computer 50. Computer 50 is also coupled to detection device 40, by link 59. Detection device 40 detects the radiant energy emitted from structure 20 due to the heating by thermal line 36.

In operation, detection device 40 is first calibrated without thermal line 36 transferring heat to structure 20. Typically, structure 20 is in equilibrium with its surroundings during calibration. Then, computer 50 instructs power supply 32 of thermal source 30 to generate a predetermined amount of power. The power generated by power supply 32 is transferred to thermal line 36 by supply line 34, which transfers heat created by the power to structure 20. Structure 20 begins to emit radiant energy due to the heating. Detection device 40, which is also controlled by computer 50, detects the radiant energy when instructed to by computer 50, usually at predetermined times. Detection device 40 uses the radiant energy received from structure 20 to determine the temperature at various points of structure 20. These temperatures are then transferred to computer 50 through link 59. Computer 50 stores the temperature at the various points in table 56 of memory 54. Then, processor 52 can create a thermal signature of structure 20 based on the temperature determinations. This thermal signature can be compared with a predetermined baseline thermal signature of structure 20 to determine whether any anomalies exist.

In particular embodiments, detection device 40 can determine the temperature at various points of structure 20 at several different times. Computer 50 can use these temperature measurements to form a thermal signature of structure 20 at each time. Thus, computer 50 can generate a thermal signature of structure 20 that varies with time. In a particular embodiment, computer 50 can compare a predetermined baseline thermal signature with a generated thermal signature by use of data fitting procedures or pattern recognition to quickly determine the defect type and size.

Structure 20 can be a wing of an aircraft, a fuselage of an aircraft, a landing gear of an aircraft, or any other structural component. Furthermore, structure 20 can be solid, have a passage, such as passage 26, have internal cavities, or have any other structural shape. Structure 20 can be composed of metal, plastic, or composite.

Power supply 32 of thermal source 30 can be an electrical source, such as an electrical generator, and supply line 34, thermal line 36, and supply line 38 can be electrically conductive elements. Thus, when power supply 32 generates power, a current is produced in thermal line 36. Due to the current, thermal line 36 produces heat due to the power it dissipates because of its resistance. This heat is transferred to structure 20, heating it. In some embodiments, thermal line 36 is embedded in structure 20, between outer surface 22 and interior surface 24.

Detection device 40 can be any of a variety of devices well known in the art for detecting radiant energy emitted from a structure. In a particular embodiment, detection device 40 can be an infrared (IR) detection device, which are well known to those of skill in the art.

Processor 52 of computer 50 can be a complex instruction set computer (CISC), a reduced instruction set computer (RISC), or any other device that can electronically manipulate electronic information. Memory 54 can be random access memory (RAM), read-only memory (ROM), compact disk read-only memory (CD-ROM), or any other electronic or optical volatile or nonvolatile computer memory. In particular embodiments, computer 50 does not control thermal source 30 and/or detection device 40.

In the embodiments where thermal line 36 is an electrically conductive element, thermal line 36 can have a homogeneous or a nonhomogeneous resistivity. If thermal line 36 has a homogeneous resistivity, it will produce substantially the same amount of heat throughout structure 20. If, however, thermal line 36 has a nonhomogeneous resistivity, thermal line 36 will produce different amounts of heat at different points of structure 20, the higher amounts occurring where the resistivity is higher. The latter configuration of thermal line 36 is useful in targeting critical areas of structure 20, such as stress concentrations, for heating. A variety of well known thermal modeling programs can be used to aid in determining the thermal signatures of structure 20 to optimize the heat output of thermal source 30. In addition, the current produced in thermal line 36 can be in several forms. For example, the current produced may be in a single pulse, to resemble a flash excitation. Additionally, a steady state current may be produced, providing a steady transfer of heat to structure 20.

A technical advantage of locating thermal line 36 within structure 20 is that the heat from thermal source 30 is transferred to the inside of structure 20. Thus, defects that are buried deep within structure 20, hidden if structure 20 is complex, or in their incipiency, which can all affect the thermal signature, are heated, allowing for them to be detected and analyzed. Another technical advantage is that the amount of heat transferred to structure 20 can be accurately controlled, providing a more accurate determination of the defects. In addition, having thermal source 30 at least partially within structure 20 allows ready testing of structure 20 in the field. Thus, the invention is useful in manufacturing testing, routine maintenance, and servicing of aircraft parts.

FIG. 2A illustrates a configuration of structure 20 for certain embodiments where thermal line 36 is an electrically conductive element embedded in structure 20. In these embodiments, structure 20 includes a web 60 of interwoven fibers 62–64. Fibers 62 have generally the same composition and are oriented in the same general direction in web 60. Fibers 64 also have the same general composition as fibers 62, but have a different orientation than fibers 62. Fiber 63, on the other hand, is composed of a different material than fibers 62 or fibers 64, although it is oriented in the same general direction as fibers 62. Generally, fibers 62 and fibers 64 are poor electrical conductors, but fiber 63 is a good electrical conductor. Thus, fiber 63 is a type of thermal line 36, although it is a part of structure 20. Note, in these embodiments, web 60 would generally be adhered to a number of other webs by a resin to facilitate the creation of structure 20.

In operation, power supply 32 would be coupled to fiber 63 and produce an electrical current in it. Because fiber 63 is electrically conductive, current will flow through it, and it will convert electrical energy into heat due to its resistance. The heat is transferred to structure 20.

Fibers 62 and fibers 64 can be composed of fiberglass, plastic, composite, or any other type of material that can be formed into a fiber that can be woven and have a poor electrical conductivity. Fiber 63, however, can be composed of graphite, carbon, copper, or any other type of material that may be formed into a fiber that can be woven and have a good electrical conductivity.

Figure 2B:
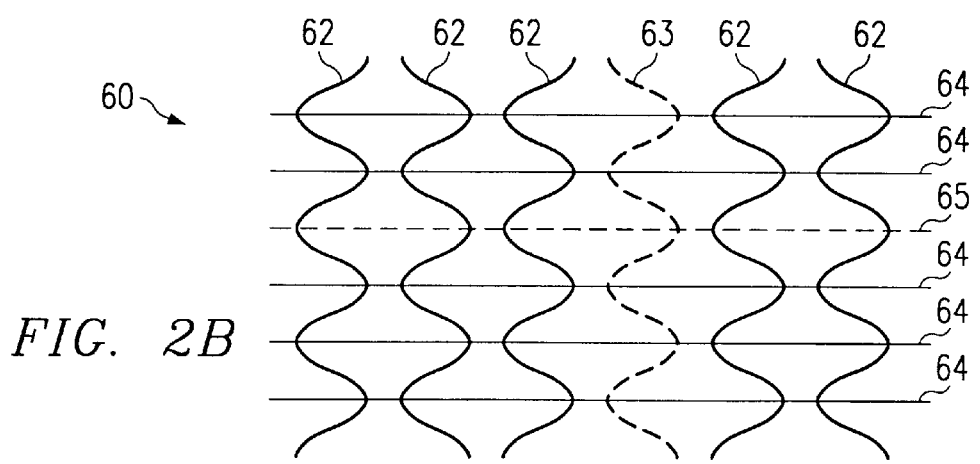
FIG. 2B represents another configuration of the structure that can be readily evaluated.

FIG. 2B shows another configuration of structure 20 for certain embodiments where thermal line 36 is an electrically conductive element embedded in structure 20. As in FIG. 2A, web 60 includes fibers 62–64. However, fibers 62 have an alternative weave pattern not present in FIG. 2A. In addition, web 60 of this configuration also includes a fiber 65. Fiber 65 is of generally the same composition as fiber 63, but is oriented in the same direction as fibers 64.

In operation, power supply 32 would be coupled to either fiber 63 or fiber 65 and would produce a current in the one to which it was coupled. In addition, power supply 32 could be coupled to both fiber 63 and fiber 65. Coupling power supply 32 to fiber 63 and fiber 65 would allow thermal stimulation of the gap between the fibers.

Figure 2C:
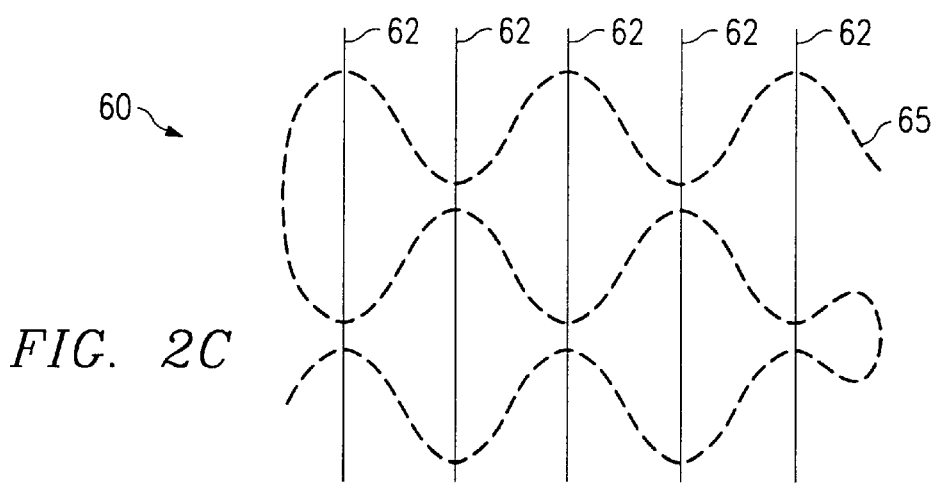
FIG. 2C represents a third configuration of the structure that can readily be evaluated.

FIG. 2C illustrates another configuration of structure 20 for certain embodiments where thermal line 36 is an electrically conductive element embedded in structure 20. As in FIG. 2B, this configuration includes a plurality of fibers 62 oriented in generally the same direction. In this embodiment, however, fiber 65 is interwoven around fibers 62 in a continual looping manner. In operation, a current would be produced in fiber 65, heating it and structure 20.

Although a variety of configurations for embedding at least part of thermal source 30 in structure 20 by interweaving an electrically conductive fiber into web 60 have been discussed, a variety of other configurations for interweaving an electrically conductive fiber into web 60 are possible. For example, multiple electrically conducting fibers could be woven into a web with the same orientation. In addition, although the discussion of configurations for embedding at least part of thermal source 30 in structure 20 have centered around interweaving an electrically conductive fiber into web 60, a variety of other configurations exist for embedding at least part of thermal source 30 in structure 20. For example, thermal line 36 could be molded into structure 20, or cavities could be created in structure 20 for thermal line 36. Further, although embedding thermal line 36 in structure 20 has been discussed with respect to locating at least part of thermal source 30 in structure 20, locating of at least part of thermal source 30 in structure 20 may be accomplished in a variety of other manners. For example, if it is not possible to embed thermal line 36 in structure 20, thermal line 36 can be laminated to an interior of structure 20, such as interior surface 24. Thus, system 10 contemplates any arrangement for locating at least part of thermal source 30 within structure 20 so that heat can be transferred to the interior of structure 20.

FIG. 3 is a flowchart 100 demonstrating one method for evaluating structure 20. The method begins at block 104 with locating a thermal source, such as thermal source 30, at least partially inside structure 20. Then, at least one predetermined baseline thermal signature of structure 20 is generated at block 108. The baseline thermal signature may be of an ideal structure, of a reference model, or of the actual structure at an earlier time. The baseline thermal signature of an ideal structure may be generated by any of a variety of well known thermal modeling programs. Then, detection device 40 is located outside structure 20 at block 112. Next, a predetermined amount of heat is generated with the thermal source at block 116. After this, detection device 40 detects the radiant energy emitted from various points of structure 20 at block 120, from which detection device 40 determines the temperature at various points of structure 20 at block 124. After this, computer 50 determines whether the time period for detecting the temperature at various points of structure 20 has expired at block 128. If the time period for detecting has not expired, computer 50 determines whether it is time for another detection at block 132. If it is not time for another detection at block 132, computer 50 determines whether the time for detecting has expired at block 128. If the time for detecting has not expired when it is time for another detection at block 132, computer 50 instructs detection device 40 to make another detection in accordance with blocks 120 and 124, as previously discussed.

When the time period for making detections with detection device 40 has expired at block 128, computer 50 generates a thermal signature at block 136 based on each detection made by detection device 40. After this, the generated thermal signature can be compared with the predetermined baseline thermal signature of structure 20 at block 140. Then, at block 144, it can be determined whether anomalies exist in structure 20.

Although several embodiments of the invention have been discussed, the invention could be composed in a variety of other manners. For example, detection device 40 could be a collection of thermocouples, thermistors, or resistance temperature devices (RTDs) located inside structure 20. Each of the thermocouples, thermistors, and/or RTDs would determine the temperature at a point of structure 20. Computer 50 could then use the determinations from these devices to generate a thermal signature of structure 20. Thermocouples may be especially useful in monitoring deeply embedded parts in structure 20 and for efficient field testing of structure 20. In fact, testing with thermocouples could even occur while the structure is in use. Thus, the invention contemplates using any devices as detection device 40 that are able to determine the temperature at various points of structure 20.

In addition, thermal source 30 does not have to rely on the dissipation of heat due to electricity to heat structure 20. For example, in particular embodiments, power supply 32 could be a heater that heats a liquid that is circulated through structure 20 through thermal line 36, which would be a liquid conduit in these embodiments. The heated liquid would conduct heat to thermal line 36, which would transfer it to structure 20, heating it. Thus, the invention contemplates using any combination of power supply and thermal transfer device that can heat structure 20 as thermal source 30. Moreover, thermal source 30 could be completely contained within structure 20, allowing structure 20 to be evaluated while in operation.

Further, although system 10 has been described as useful for evaluating defects in aircraft parts, system 10 could also be useful for evaluating defects in a variety of other structures. For example, system 10 could be useful for evaluating structural defects in helicopters, cars, trucks, airplanes, and buildings.

Although several embodiments have been disclosed for the invention, a variety of transformations, alterations, and substitutions, may be readily suggested to one skilled in the art. It is intended that any of these readily suggested transformations, alterations, or substitutions be encompassed within the scope of the appended claims.

What is claimed is:

1. A system for evaluating a structure, the system comprising:
   a) a structure to be evaluated, the structure having a predetermined baseline thermal signature and formed from a web of interwoven fibers including at least one electrically conductive fiber;
   b) a thermal source comprising a power-supply and the at least one electrically conductive fiber, the power supply operable to supply power to the at least one electrically conductive fiber to heat the structure;
   c) a detection device operable to detect a thermal energy at various points of the structure; and
   d) a computer coupled to the detection device, the computer operable to generate a thermal signature of the structure based on the thermal energy at the various points; and
   e) wherein the generated thermal signature of the structure is compared to the baseline thermal signature of the structure to determine whether anomalies exist in the structure.

2. The system of claim 1, wherein the computer is coupled to the power supply and is operable to direct the power supply to produce a steady-state current in the electrically conductive fiber.

3. The system of claim 1, wherein the web of interwoven fibers are coupled to one another with a resin.

4. The system of claim 3, wherein the electrically conductive fiber comprises graphite.

5. The system of claim 1, wherein the electrically conductive fiber is laminated to an interior surface of the structure.

6. The system of claim 1, wherein the electrically conductive fiber has a nonhomogeneous resistance, the nonhomogeneous resistance causing the heat output of the electrically conductive fiber to vary between different locations of the structure.

7. The system of claim 1, wherein the detection device comprises an infrared detection device located outside the structure, the infrared detection device capable of detecting infrared radiation emitted from the structure.

8. The system of claim 1, wherein the detection device comprises a thermocouple located inside the structure.

9. The system of claim 1, wherein the baseline thermal signature is representative of a non-defective structure.

10. The system of claim 1, wherein the computer is further operable to compare the generated thermal signature with the baseline thermal signature.

11. The system of claim 10, wherein the computer is further operable to determine if an anomaly exists in the structure.

12. The system of claim 1, wherein the computer is coupled to the power supply and is operable to direct the power supply to generate a predetermined amount of power to the at least one electrically conductive fiber.

13. The system of claim 1, wherein the at least one electrically conductive fiber is interwoven in a continual looping manner.

14. The system of claim 1, wherein the computer is coupled to the power supply and is -operable to direct the power supply to produce a single pulse current in the electrically conductive fiber.

15. A method for evaluating a structure, the method comprising:
   determining an amount of heat to be transferred to the structure;
   generating the amount of heat within the structure by directing, by a computer, a power source to deliver a corresponding amount of power to an electrically conductive fiber located at least partially inside the structure;
   detecting the thermal energy at various points of the structure;
   generating a thermal signature of the structure based on the thermal energy at the various points; and
   comparing the generated thermal signature of the structure to a predetermined baseline thermal signature of the structure.

16. The method of claim 15, wherein the electrically conductive fiber comprises graphite and is embedded in the structure.

17. The method of claim 15, wherein detecting the thermal energy at various points of the structure is performed by an infrared detection device located outside the structure, the infrared detection device capable of detecting infrared radiation emitted from the structure.

18. The method of claim 15, wherein detecting the thermal energy at various points of the structure is performed by thermocouples located inside the structure.

19. The method of claim 15, wherein the baseline thermal signature is representative of a non-defective structure.

20. The method of claim 15, further comprising determining whether anomalies exist in the structure.

21. The method of claim 15, further comprising:
   varying the amount of heat within the structure over time; and
   generating the thermal signature of the structure that varies with time.

22. A system for evaluating a structure, the system comprising:
   a structure to be evaluated, the structure formed from a web of interwoven fibers coupled together by a resin;
   at least one electrically conductive fiber associated with the web of interwoven fibers;
   a power supply coupled to the at least one electrically conductive fiber, the power supply operable to supply power to the at least one electrically conductive fiber to heat the structure;
   a detection device operable to detect a thermal energy at various points of the structure; and
   a computer coupled to the detection device, the computer operable to generate a thermal signature of the structure based on the thermal energy at the various points.

* * * * *